United States Patent [19]

Yang et al.

[11] Patent Number: 5,576,008
[45] Date of Patent: Nov. 19, 1996

[54] PREPARATION OF PESTICIDE MICROCAPSULE

[75] Inventors: Chien-Chun Yang; I-Horng Pan, both of Hsinchu, Taiwan

[73] Assignee: Industrial Technology Research Institute, Taiwan

[21] Appl. No.: 262,850

[22] Filed: Jun. 21, 1994

Related U.S. Application Data

[63] Continuation of Ser. No. 857,265, Jul. 19, 1991, abandoned.

[51] Int. Cl.⁶ .................................................... A01N 25/28
[52] U.S. Cl. ...................... 424/408; 424/496; 424/502; 264/4.1; 264/4.7; 427/213.3; 514/963
[58] Field of Search ..................................... 424/449, 450, 424/408, 489, 418–420, 496, 502; 264/4.32, 4.3, 4.1; 428/402.2; 427/213.3; 514/963

[56] References Cited

U.S. PATENT DOCUMENTS

| | | | |
|---|---|---|---|
| 3,516,846 | 6/1970 | Matson | 503/215 |
| 3,993,831 | 11/1976 | Vassiliades | 428/321.5 |
| 4,001,140 | 1/1977 | Foris et al. | 252/316 |
| 4,089,802 | 5/1978 | Foris et al. | 252/316 |
| 4,353,809 | 10/1982 | Hoshi et al. | 252/316 |
| 4,394,287 | 7/1983 | Scarpelli | 64/4.32 |
| 5,160,529 | 11/1992 | Scher et al. | 71/118 |

FOREIGN PATENT DOCUMENTS

| | | |
|---|---|---|
| 44-014379 | 6/1969 | Japan . |
| 45-029483 | 3/1970 | Japan . |
| 46-30282 | 9/1971 | Japan . |
| 52-018671 | 5/1977 | Japan . |
| 62-149607 | 7/1987 | Japan . |

*Primary Examiner*—Neil S. Levy
*Attorney, Agent, or Firm*—Darby & Darby, P.C.

[57] ABSTRACT

This invention relates to a novel method for preparing pesticide microcapsules in which the release rate and the release period of the pesticide are controlled. A process has been discovered for encapsulating a trace amount of pesticide with a urea-formaldehyde resin, mechanically stirring the resin in the presence of vegetable oil and the pesticide and reacting the mixture under suitable conditions to form a desired pesticide microcapsule.

18 Claims, No Drawings

5,576,008

PREPARATION OF PESTICIDE MICROCAPSULE

This is a continuation of application Ser. No. 07/857,265, filed Jul. 19, 1991, abandoned.

BACKGROUND OF THE INVENTION

This invention relates to a method for preparing a pesticide microcapsule in which the release rate and release period of the pesticide can be controlled.

There are two major conventional methods to form a urea-formaldehyde resin membrane. In the first method, a water-soluble macromolecule is prepared with urea and formaldehyde. Thereafter, the macromolecule is microemulsified with oil-soluble components to form a microcapsule. See, for instance, U.S. Pat. Nos. 3,516,846 and 3,993,831 and Japanese Patent Publications 30282/71, 29783/70, 14739/69 and 18671/77. The method which is described in U.S. Pat. No. 3,516,846 and Japanese Patent 46-30282 is suitable for encapsulating a large amount of pesticide. In this procedure, a large amount of vegetable oil is used (the amount of the oil to that of aqueous prepolymer solution is 0.38–0.48:1). Japanese Patent 45-29483 discloses a method which uses a surface tension enhancer to thoroughly disperse an oil-soluble material in water-soluble encapsulating material, so as to encapsulate the oil-soluble material and act as a surface tension enhancer. Japanese Patent 44-14739 discloses a method that dissolves the nonpolar material in a hydrophobic liquid. Small droplets of the liquid are added to an aqueous water-soluble modified urea resin solution. After a crosslinking reaction, microcapsules suitable for pressure sensitive non-carbon copy paper are formed. The additions of the non-polar material by small droplets has disadvantages in large scale production of microcapsules. In Japanese Patent 52-18671, an oil-soluble solution of formaldehyde condensate is stirred with an aqueous solution of its polymer to form a water-in-oil emulsion. A reaction at the interface is carried out to form a microcapsule. The advantage of this method is the employment of water-soluble polymer as an emulsifier instead of using a surfactant. However, this method has the disadvantage of requiring additional preparation of an oil-soluble formaldehyde condensate. Japanese Patent Publication 62-149607 describes a method which uses 3–20% of surfactant to encapsulate dispersed ethoprophos in vegetable oil by using a urea-formaldehyde resin. A large amount of oil is used in this method (1–9 parts relative to the weight of aqueous prepolymer solution) and the amount of pesticide encapsulated is more than 3.0%.

The second method comprises the simultaneous formation of microcapsule and polymerization of urea and formaldehyde, as described in U.S. Pat. Nos. 4,001,140 and 4,089,802. Both of these patents suggest that simultaneous microencapsulation and polymerization can only be done through the use of carboxyl-substituted aliphatic hydrocarbon polycharged substances having negative charges. Therefore, application of this method is very limited. In addition, U.S. Pat. No. 4,353,809 uses polyvalent isocyanates to improve the emulsifiability. However, this method is complex and hard to control in its production process.

SUMMARY OF THE INVENTION

This invention relates to a method for preparing a pesticide microcapsule in which the release rate and release period of the pesticide can be controlled. The method comprises the steps of mixing a trace amount (i.e., <1.3%) of a pesticide and a vegetable oil with an aqueous solution of a urea-formaldehyde polymer. The mixture of the prepolymer, pesticide and vegetable oil is mechanically stirred at a speed greater than 700 rpm. The vegetable oil being at a concentration of 0.1 to 0.6 grams per ml of the prepolymer. The mixture is polymerized under suitable conditions, without the presence of a surfactant, to yield a desired pesticide microcapsule.

DETAILED DESCRIPTION OF THE INVENTION

The present invention relates to a method for preparing pesticide microcapsule in which the release rate and release period of the pesticide can be controlled. The method comprises preparation of an aqueous prepolymer solution of a urea-formaldehyde resin. A suitable ratio of an oil-soluble pesticide and vegetable oil are homogeneously mixed into the prepolymer solution. The solution is mechanically stirred and set under suitable conditions so as to form a microcapsule. The setting is sufficient for forming a solid tact free coating.

There are three major factors for the production of controlled release pesticide products. The first is how to effectively control the release amount of pesticide so that the attack of pests can be effectively controlled without damage or side effects to a target subject due to an overdose of the pesticide. The second is how to effectively control the length of the release period so that the pesticide can be utilized completely. The third is how to produce the products simply and economically so that the price will be low enough to allow the products to be applied to agriculture.

Accordingly, this invention is designed on the basis of the three factors above. Essentially, the polymer matrix used in the invention is the well known urea-formaldehyde resin. In one embodiment of the invention, 24 grams of urea is mixed with 48.8 grams of a 37% formaldehyde solution. The pH of the solution is adjusted with a sodium hydroxide solution to about 8.0 to 8.3. After reacting at 70° C. for about one hour, the solution is diluted with water to obtain a 100 ml prepolymer solution.

The processing procedure comprises using a proportionable mixture of the aqueous prepolymer solution, vegetable oil and pesticide. The mixture is kept in water bath at 45°–50° C. The mixture is stirred at more than 700 rpm for 20–30 minutes to achieve a thoroughly emulsified state. The pH is adjusted with a 10% citric acid solution to about 2.0 to 6.0 for carrying out a crosslinking reaction of the prepolymer in the acid solution for about 3–6 hours. Preferably, the pH is adjusted to about 2.9–3.0. Preferably, the crosslinking reaction is carried out for about 3.5–4.5 hours. Warm water can be added during the reaction in order to maintain the volume of the solution. Finally, the reaction mixture can be poured into ice water, filtered and air dried to yield a desired pesticide microcapsule.

Vegetable oil at a concentration of 0.1 to 0.6 grams per ml of the prepolymer and pesticide at a concentration of 0.00150 to 0.0012 grams per ml of the prepolymer is added to the aqueous prepolymer solution. Under this composition and operational conditions, the pesticide can almost be completely encapsulated. The amount of vegetable oil in the above-described concentration has two functions: first, encapsulation can be performed even with a minimal amount of pesticide (the amount of the pesticide in the encapsule is less than 1.3%); and second, microcapsules having the same pesticide content can be prepared having different release rates. Thus, control of the release rate and of the release period can be achieved. The speed of stirring described above has two functions: first, a rapid emulsification effect can be obtained by stirring under high speed without the needing to add a surfactant; and second, by changing the speed of stirring, the microcapsules can be produced having the same pesticide content, but with different release rates.

The pesticides which can be used with this invention comprise an oil-soluble type. For example, allethrin, deltamethrin, permethrin, cypermethrin, chlorpyrifos and diazinon.

The invention will be more substantially illustrated with the following preparations and examples; but it shall not be limited by these examples.

Preparation of Prepolymer 24 g of urea is mixed with 48.8 g of a 37% formaldehyde solution. The pH of the solution is adjusted with a sodium hydroxide solution to about 8.0–8.3. After reacting at 70° C. for one hour, the solution is diluted with water to 100 ml.

Preparation of Microcapsule

The above aqueous prepolymer solution/vegetable oil/pesticide are mixed in constant proportion and kept in water bath at about 45°–50° C. After stirring at more than 700 rpm for 20–30 minutes, a sufficiently emulsified state is obtained. The pH of the emulsion is adjusted to about 2.9–3.0 by adding 10% citric acid solution drops so as to carry out the crosslinking reaction for 3–6 hours. A suitable amount of water should be added during the reaction to maintain its volume. Finally, the reaction mixture is poured into ice water, filtered and air dried to yield the desired microcapsule.

EXAMPLE 1

Mixtures of aqueous urea-formaldehyde prepolymer solution, soybean oil and deltamethrin are prepared in accordance with the formulations shown in Table 1 to produce microcapsules.

TABLE 1

| Treatment Number | Prepolymer Solution (ml) | Soybean oil (g) | Deltamethrin (g) |
| --- | --- | --- | --- |
| 1 | 50 | 5 | 0.1562 |
| 2 | 50 | 10 | 0.0990 |
| 3 | 50 | 10 | 0.2361 |
| 4 | 50 | 15 | 0.1188 |
| 5 | 50 | 20 | 0.1496 |
| 6 | 50 | 30 | 0.1980 |
| 7 | 50 | 10 | 0.3159 |

*The speed of stirring is 1078 rpm.

Table 2 is illustrative of the yield of the microcapsules for the corresponding formulations of Table 1. The encapsulating efficiency of the formulations is shown in Table 2.

TABLE 2

| Treatment Number | Yield (g) | Deltamethrin content (g) | Encapsulating efficiency (%) |
| --- | --- | --- | --- |
| 1 | 19.1 | 0.1332 | 85.2 |
| 2 | 23.1 | 0.099 | 100 |
| 3 | 21.1 | 0.2321 | 98.3 |
| 4 | 28.4 | 0.1192 | 100 |
| 5 | 31.9 | 0.1499 | 100 |
| 6 | 40.82 | 0.1878 | 94.8 |
| 7 | 25.9 | 0.3154 | 99.8 |

Table 3 is illustrative of the release rate of deltamethrin of the microcapsules which are prepared in accordance with the formulations described in Table 1.

TABLE 3

| Treatment Number | Deltamethrin content (ug/g) | Release rate (ug/g-day) |
| --- | --- | --- |
| 1 | 6,974 | 5.04 |
| 2 | 4,300 | 3.03 |
| 3 | 11,000 | 9.43 |
| 4 | 4,200 | 5.23 |
| 5 | 4,700 | 6.08 |
| 6 | 4,600 | 6.2 |
| 7 | 12,178 | Not tested |

The release rate was measured by suspending one gram of microcapsule with 100 ml water, and determining the deltamethrin content in the water at constant intervals.

EXAMPLE 2

The formulation of microcapsules prepared in Treatment No. 2 of Table 1 was stirred at various speeds. Table 4 shows the results and effects on the formation of the microcapsule and its release rate.

TABLE 4

| Treatment Number | Speed of stirring (rpm) | Yield (g) | Deltamethrin content (ug/g) | Release rate (ug-g-day) | Encapsulating efficiency (%) |
| --- | --- | --- | --- | --- | --- |
| 1 | 698 | 12.1 | — | — | — |
| 2 | 1078 | 23.1 | 4300 | 1.37 | 100 |
| 3 | 1540 | 23.5 | 4400 | 2.99 | 100 |

EXAMPLE 3

Microcapsules were prepared as described in Example 1 except that allethrin was used instead of deltamethrin. The formulations used are shown in Table 5.

TABLE 5

| Treatment Number | Prepolymer solution (ml) | Soybean oil (g) | Allethrin (g) |
| --- | --- | --- | --- |
| 1 | 50 | 10 | 0.1190 |
| 2 | 50 | 20 | 0.1680 |
| 3 | 50 | 30 | 0.2520 |

*The speed of stirring is 1078 rpm.

Table 6 shows yield and encapsulating efficiency of the formulation of the microcapsules described in Table 5.

TABLE 6

| Treatment Number | Yield (g) | Allethrin content (g) | Encapsulating efficiency (%) |
| --- | --- | --- | --- |
| 1 | 17.9 | 0.1177 | 98.9 |
| 2 | 23.1 | 0.1683 | 100 |
| 3 | 28.8 | 0.2502 | 99.3 |

Table 7 shows the release rate of the formulations of the microcapsules shown in Table 5.

TABLE 7

| Treatment Number | Allethrin content (ug/g) | Release rate (ug/g-day) |
| --- | --- | --- |
| 1 | 6,573 | 6.91 |
| 2 | 7,286 | 14.57 |
| 3 | 8,687 | 36.96 |

EXAMPLE 4

This example illustrates the biological evaluation of the microcapsule of the invention by comparing its control ability against *Sitophilus zeamais* in warehouse with those of microcapsule prepared by encapsulating with other resins under the same 0.5% content of the pesticide. The results are shown in Table 8.

TABLE 8

| Encapsulating Material | Pesticide content (%) | Mixing ratio* | Pest Control Efficiency (%) after ( month) | | | | |
| --- | --- | --- | --- | --- | --- | --- | --- |
| | | | 1 | 2 | 3 | 6 | 8 |
| Urea-formaldehyde resin | 0.5 | 1000 | 74.1 | 84.8 | 99 | 100 | 94.8 |
| Polysulfone | 0.5 | 1000 | 0.3 | 0 | 2 | 20.9 | 3.6 |
| Polycarbonate | 0.5 | 1000 | 0.2 | 0.2 | 0 | 23.4 | 14.18 |

*Ratio of corn to microcapsule.

From the results shown in Table 8, an outstanding improvement was obtained in pest control efficiency of the microcapsule of the invention as compared to the other encapsulating materials.

What is claimed is:

1. A method for preparing a pesticide microcapsule comprising the steps consisting essentially of:

adding to an aqueous urea-formaldehyde prepolymer a vegetable oil and up to 1.3% of the final weight of the microcapsule of an oil-soluble pesticide to form a solution, the amount of vegetable oil added being from about 0.1 to 0.6 gram per ml. of prepolymer, said oil-soluble pesticide being allethrin, deltamethrin, permethrin, cypermethrin, chlorpyrifos, or diazinon and further being added to said solution in an amount of from about 0.0015 to about 0.0063 gram per ml of the prepolymer;

mixing said solution in a water bath at 40°–50° C. at a speed greater than 700 RPM to achieve a thoroughly emulsified state;

adding an acid to said solution to acidify said solution to a pH of between about 1 and 6; and crosslinking the urea-formaldehyde prepolymer in said acidified solution, in the absence of a surfactant, for a period of from 3 to 6 hours to produce a pesticide microcapsule having a predetermined release rate and release period.

2. The method according to claim 1, wherein the amount of said vegetable oil added to said solution is from about 0.2 to about 0.4 grams per ml of prepolymer.

3. The method according to claim 1, wherein said vegetable oil is soybean oil.

4. The method according to claim 1, wherein said oil-soluble pesticide is allethrin or deltamethrin.

5. The method according to claim 1, wherein said solution is acidified to a pH between about 2.9 and 3.0.

6. The method according to claim 1, wherein the mixing takes place for from 20 to 30 minutes.

7. A pesticide microcapsule prepared by the steps consisting essentially of:

adding to an aqueous urea-formaldehyde prepolymer, a vegetable oil and up to 1.3% of the final weight of the microcapsule of an oil-soluble pesticide to form a solution, the amount of vegetable oil added being from about 0.1 to 0.6 gram per ml, of prepolymer, said oil-soluble pesticide being allethrin, deltamethrin, permethrin, cypermethrin, chlorpyrifos, or diazinon and further being added to said solution in an amount of from about 0.0015 to about 0.0063 gram per ml of the prepolymer;

mixing said solution in a water bath at 40°–50° C. at a speed greater than 700 RPM to achieve a thoroughly emulsified state;

adding an acid to said solution to acidify said solution to a pH of between about 1 and 6; and crosslinking the urea-formaldehyde prepolymer in said acidified solution, in the absence of a surfactant, for a period of from 3 to 6 hours to produce a pesticide microcapsule having a predetermined release rate and release period.

8. The pesticide microcapsule according to claim 7, wherein the amount of said vegetable oil added to said solution is from about 0.2 to about 0.4 grams per ml of prepolymer.

9. The pesticide microcapsule according to claim 7, wherein said vegetable oil is soybean oil.

10. The pesticide microcapsule according to claim 7, wherein said oil-soluble pesticide is allethrin or deltamethrin.

11. The pesticide microcapsule according to claim 7, wherein said solution is acidified to a pH between about 2.9 and 3.0.

12. The pesticide microcapsule according to claim 7, wherein the mixing takes place for from 20 to 30 minutes.

13. A method for controlling pests which comprises applying to an area containing or potentially containing pests microcapsules prepared by the steps consisting essentially of:

adding to an aqueous urea-formaldehyde prepolymer a vegetable oil, and up to 1.3% of the final weight of the microcapsules of an oil-soluble pesticide to form a solution, the amount of vegetable oil added being from about 0.1 to 0.6 gram per ml. of prepolymer, said oil-soluble pesticide being allethrin, deltamethrin, permethrin, cypermethrin, chlorpyrifos, or diazinon and further being added to said solution in an amount of from about 0.0015 to about 0.0063 gram per ml of the prepolymer;

mixing said solution in a water bath at 40°–50° C. at a speed greater than 700 RPM to achieve a thoroughly emulsified state;

adding an acid to said solution to acidify said solution to a pH of between about 1 and 6; and crosslinking the urea-formaldehyde prepolymer in said acidified solution, in the absence of a surfactant, for a period of from 3 to 6 hours to produces pesticide microcapsules having a predetermined release rate and release period to an environment susceptible to pests.

14. The method according to claim 13, wherein the amount of said vegetable oil added to said solution is from about 0.2 to about 0.4 grams per ml of prepolymer.

15. The method according to claim 13, wherein said vegetable oil is soybean oil.

16. The method according to claim 13, wherein said oil-soluble pesticide is allethrin or deltamethrin.

17. The method according to claim 13, wherein said solution is acidified to a pH between about 2.9 and 3.0.

18. The method according to claim 13, wherein the mixing takes place for from 20 to 30 minutes.

* * * * *